United States Patent
Kobashigawa et al.

[19]

[11] Patent Number: 5,829,979
[45] Date of Patent: Nov. 3, 1998

[54] REINFORCING MATERIAL FOR DENTAL APPLIANCES AND PROSTHESES

[75] Inventors: Alvin I. Kobashigawa, Laguna Beach; Jeffrey D. Roe, Phillips Ranch, both of Calif.

[73] Assignee: The Kerr Corporation, Orange, Calif.

[21] Appl. No.: 603,545

[22] Filed: Feb. 20, 1996

[51] Int. Cl.[6] ........................................ A61C 5/00
[52] U.S. Cl. ............................ 433/180; 433/215
[58] Field of Search .................... 433/180, 223, 433/226, 229, 215

[56] References Cited

U.S. PATENT DOCUMENTS

| | | | |
|---|---|---|---|
| 4,172,323 | 10/1979 | Orlowski | 433/180 |
| 4,410,586 | 10/1983 | Ladizesky et al. | |
| 4,504,229 | 3/1985 | Garito et al. | |
| 4,717,341 | 1/1988 | Goldberg et al. | |
| 4,728,291 | 3/1988 | Golub | 433/223 |
| 4,867,683 | 9/1989 | Meisel | 433/180 |
| 5,098,304 | 3/1992 | Scharf | 433/180 |
| 5,102,332 | 4/1992 | Uthoff | |
| 5,176,951 | 1/1993 | Rudo | 433/180 |
| 5,304,421 | 4/1994 | Lamy et al. | |

FOREIGN PATENT DOCUMENTS

| | | |
|---|---|---|
| 0292026A2 | 11/1988 | European Pat. Off. |
| 0575960A1 | 12/1993 | European Pat. Off. |
| 0706876A1 | 4/1996 | European Pat. Off. |
| WO93/13733A1 | 7/1993 | WIPO |
| WO96/26687A1 | 9/1996 | WIPO |

OTHER PUBLICATIONS

Plasma Science, Technical Notes, pp. 1–8, "Gas Plasma Treatment Of Spectra® Fiber" by S. L. Kaplan, et al., published Mar. 7, 1988.
Plasma Science, Technical Notes, pp. 1–5, "Plasma Surface Treatment of Plastics To Enhance Adhesion: An Overview" by Stephen L. Kaplan, et al., published Feb., 1990.
Trends & Techniques, "A Technique for Fabricating A Reinforced Composite Splint" by Kingsley Kau, CDT and David N. Rudo, D.D.S., Nov., 1992, pp. 31–33.
Reality Now, The Information Source For Aesthetic Dentistry, The Ratings, "Ribbond", published Mar. 1993, No. 4, pp. 1–3.
Brochure of Ribbond, Inc. entitled "Ribbond®" published in 1993.

*Primary Examiner*—Ralph A. Lewis
*Attorney, Agent, or Firm*—Wood, Herron & Evans, L.L.P.

[57] ABSTRACT

An ultra high strength plastic mesh reinforcing material for forming a dental appliance or prosthesis, a method of fabricating a prosthesis therewith and a dental prosthesis made thereby are provided. The material is in the shape of a ribbon and formed of fibers, preferably of ultra high strength polyethylene, that are woven into a matrix in which yarns of the fibers preferably extend at angles to the transverse extent of the ribbon to permit the ribbon to be shaped through the adjusting of its width by a practitioner. Such yarns are preferably braided, so that diagonally angled fibers will result and no fibers are cut along the edges of the ribbon. The braid is preferably a two-over/two-under pattern that utilizes an odd number of carriers. The fibers are preferably surface activated, such as by a cold plasma treatment to enhance adherence of resin of which the appliance or prosthesis is formed.

19 Claims, 4 Drawing Sheets

REINFORCING MATERIAL FOR DENTAL APPLIANCES AND PROSTHESES

This invention relates to fabric material for reinforcing resins used in dentistry, and, more particularly, to plastic reinforcing material matrices for use in restorative dental procedures, appliances and prostheses.

BACKGROUND OF THE INVENTION

Reinforcing fibrous plastic materials are finding increasing use in dentistry. Such uses include the making of dental repairs, the formation of orthodontic retainers, the making of temporary, fixed and removable composite bridges and other dental prostheses, and the splinting of mobile teeth in orthodontic and periodontal treatment. Typically, fibers of ultra high strength polymer material are embedded in settable restorative resins and a dental structural device is formed, either on or off of a patient's teeth, and the resin is then cured. The ultra high strength plastics, as that term is used herein for such structural devices, include materials, usually highly molecularly oriented extended chain polymers, that are stronger than steel, lighter than glass and absorb considerable energy before breaking. These materials have high strength, or high resistance to initial fracture, and a high modulus of elasticity, or resistance to elongation when stressed. Such ultra high strength plastics currently known and used include aromatic polyamide fibers, or aramids, such as poly-p-phenyleneterephthalamide, which is manufactured by Dupont under its trademark Kevlar and ultra high molecular weight, extended chain highly oriented polyethylene fibers, manufactured by Allied Signal under its trademark Spectra.

For certain uses, reinforcing meshes or matrices of plastic material have been provided in the form of narrow thin ribbons, which are cut to desired lengths, immersed in a low viscosity restorative thermosetting resin such as that manufactured by Kerr Corporation under its trademark Porcelite. The resin impregnated ribbon is then extended over a form or model or across a tooth of a patient, or over a preformed composite core, in one or more layers. The resin is then cured, for example, by exposure to ultraviolet light. The reinforcing material is sometimes pretreated with a cold gas plasma or other such process that will increase the wetability and chemical activity of the material and thereby enhance the ability of the material and the resin to adhere.

Of the desired properties of such reinforcing ribbon are its strength, which include its resistance to initial fracture when subjected to stress, its ability to carry high stress prior to ultimate failure, its ability to deform or undergo substantial strain prior to failure, and its ability to absorb considerable energy as it is deformed under stress prior to its ultimate failure. Further, in order to reliably avoid loss of its design strength by an unraveling of the fibers prior to its formation with the resin, the reinforcing material is preferably woven or otherwise processed to prevent an unraveling of the fibers, particularly at its edges, which would reduce the effective load carrying cross-section of the material. The unraveling, for example, along the long edges of a narrow ribbon of the material could substantially reduce its effective width.

In addition, it is desirable that the material be easy to form to various shapes and contours in the molding process without the continued application of external force to hold the material in place until the resin is cured. Thus, the material should not be of such a type that will rebound or elastically return to previous shape once put in place by the practitioner. This property is often referred to as that of low material memory.

One such ribbon-like product, as well as its manufacture and use, has been described in U.S. Pat. No. 5,176,951 to Rudo entitled "Reinforced Dental Appliances and Prostheses", which is hereby expressly incorporated into this background discussion as well as the detailed description of the invention below. A product made in accordance with this patent is manufactured by Ribbond, Inc. under the trademark Ribbond, the properties and uses of which are discussed in the March 1993 (Number 42) issue of "Reality Now" published by Reality Publishing Company, Houston, Tex., pp. 1–4, similarly incorporated herein by reference. This product is made of the Spectra® brand of polyethylene fibers woven in a loose 30×30 leno weave and treated with a cold plasma.

Notwithstanding the developments of the prior art, there are limitations to the strength, unravelability and conformability (low memory) of the reinforcing materials provided for dental use, which have resulted in compromises of the properties desired. Accordingly, a need remains for a reinforcing material that is strong, conforms in molding without rebound, and will retain its weave at the edges.

SUMMARY OF THE INVENTION

A primary objective of the present invention is to provide a reinforcing matrix material for use in dental appliances, prostheses and procedures that overcomes the limitations of, and improves upon, the prior art.

It is a more particular objective of the present invention to provide a reinforcing woven ultra high strength plastic material that can be provided in ribbon form that will retain its weave along its edges.

It is a further objective of the present invention to provide a reinforcing woven reinforcing material, particularly an ultra high strength plastic material, that possesses a low material shape memory and that is otherwise easy for a dental practitioner to form and handle. Particularly, it is an objective of the present invention to provide a reinforcing interwoven material, particularly an ultra high strength plastic material, in the form of a ribbon that can be widened or narrowed or otherwise adjusted in width or other dimension to effectively correspond to the width or other dimension of the structure or portion thereof to be reinforced.

In accordance with the present invention, there is provided reinforcing material made of a matrix of fibers or yarns of high strength polymer, preferably ultra high strength plastic, interwoven, and preferably braided, into a ribbon that is useful in strengthening resin formed dental appliances or prostheses. By "braided" is meant an array of alternating sets of fibers or threads that usually extend diagonally, or at a substantial angle, across the ribbon, preferably crossing the longitudinal or lengthwise extent of the ribbon at angles of preferably between 25° and 45°. In closeup, such a braid may appear as a rotated woven pattern, with the crossing fibers perhaps, but not necessarily perpendicular to each other. Such a braid is formed by a process, by which one does not normally distinguish warps from wefts as one would with fabric woven on a loom. Rather the braiding process is one carried out on a braiding machine by which one or more warp-like "ends" or longitudinal fibers of continuous filament yarn are combined, the yarn having an odd number of carriers and preferably braided into a two-over/two-under weave pattern. The construction of the material may be referred to as "flat braided". The term "interwoven" is used herein to refer to the resulting pattern of fibers, whether produced by a process resulting in fabric commonly referred to as "woven" or "braided".

In the preferred embodiment of the invention, ultra high strength plastic material is provided in the shape of a ribbon having a longitudinal or lengthwise extent, with the fibers inclined to the longitudinal axis of the ribbon at an angle of from about 25° to about 45°. Such an angled orientation of the fibers enhances the ability of the ribbon to be widened, narrowed, or otherwise dimensionally adjusted, as required, to most effectively reinforce the full desired extent of the dental structure being formed. While braiding of the ribbon is an effective and preferred manner of achieving a reinforcing matrix of fibers that are configured and oriented the transverse adjustment of the width of the ribbon, providing other fiber configurations that do not require straight transverse yarns to resist transverse stretching of the ribbon, for example, may also accomplish the variable width objective. In the preferred embodiment of the invention, crossing sets of fibers both extend at angles to both the transverse and longitudinal extent of the ribbon to facilitate a widening or narrowing of the ribbon by respectively applying transverse or longitudinal tension to the ribbon.

Preferably, rather than being cut at the parallel side edges of the ribbon, the fibers alternately reverse transverse direction at each of the edges and continue along the length of the ribbon, thereby preventing an unraveling of the weave or braid at the edges. Alternatively, to avoid edge unraveling, the ribbon may be in the form of a tube with the fibers continuing, half clockwise and half counterclockwise, around the tube along its entire length. The tube is normally flattened to take on the shape of a two layer ribbon. The weave is preferably a tight weave comparable to a plain weave of 50×50 fiber construction. The ribbon, once formed, is treated in a way that will activate the ribbon surface to facilitate its adhesion to a resin. Such a treatment is preferably a cold plasma treatment that will enhance the chemical activity of atoms on the fiber surfaces and thereby enhance the adhesion of the fibers to a resin when immersed therein.

Further, according to the preferred embodiment of the present invention, a narrow ribbon of fabric of, for example, from 1 mm to 5 mm in width, is formed of braided yarns of high tenacity, ultra high molecular weight, gel spun continuous filament polyethylene fiber, such as Spectra® fiber produced by Allied Signal, Inc. The fiber is preferably flat braided and in a two over two under pattern. For nominally 3 mm wide ribbon, the specifications of such ribbon is 17 ends, for example, of 215 denier Spectra® fiber 18 PPI (picks per inch) with a break strength of at least 125 pounds (125SFB17 Spectra® flat braid). The braid is preferably provided in a two over two under pattern.

It is further preferred that the yarns or fibers extend in a first diagonal direction parallel to one another, crossing opposing fibers that extend in a second diagonal direction, also parallel to one another, and generally transverse the first direction, in a two over two under pattern, then, upon reaching an edge of the ribbon, each fiber folds back and forms one of the crossing elements that extends in the second diagonal direction, crossing in a two over and two under pattern the parallel fibers that are extending in the first diagonal direction. This recurring zigzag pattern is sometimes regarded as a characterizing difference between a weave, with its distinct warps and wefts, and a braid with its single set of continuous filaments. Unlike an ordinary weave, for example, where wefts can unravel unless otherwise locked in some manner, the braid presents no unraveling problem. Similarly, in an alternative embodiment, the braid can be formed as a tube, with the filaments of the braid divided into two sets, one spiraling clockwise and one counterclockwise. Such a tube, laid flat, forms a two layer ribbon which also presents no edge unraveling problem.

The reinforcing material, when in a braided weave, particularly a two over two under weave, contains an array of spaces or voids that make space for the resin, thereby allowing an effective bonding between the resin and the fibers. In addition, the braided material is highly formable by a dental practitioner, can be wrapped over a tooth or other structure without rebounding to its original shape when released, and can be manipulated to widen or narrow the ribbon. Further, the ability of the material to be widened or narrowed facilitates the working of the resin into the material in a way that is not seen with leno and other such weaves.

With the invention as described herein, a stronger reinforcing material is provided for dental appliance and prostheses use and other treatments. The material is provided in the form of a ribbon that is not prone to unraveling at the edges. Further, the material when used with a resin has less memory, and is therefore more effective to form, than previous reinforcing materials provided for dental purposes.

These and other objectives and advantages of the present invention will be more readily apparent from the following detailed description of the of the preferred embodiments of the invention, in which:

DETAILED DESCRIPTION OF THE PREFERRED EMBODIMENT

Figure 1:
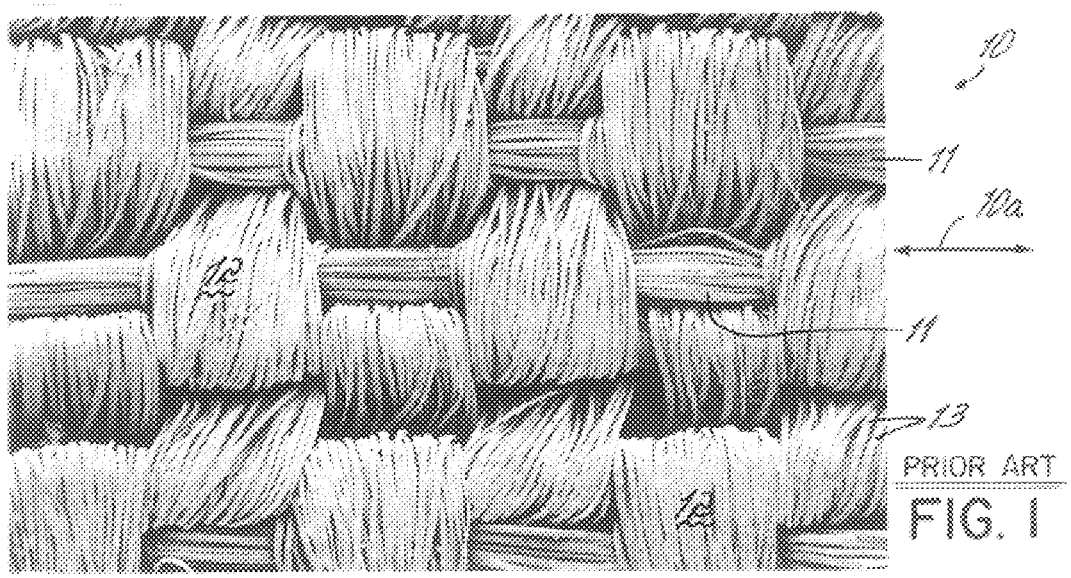
FIG. 1 is a SEM photographic enlargement of a commercial embodiment of a prior art reinforcing material as disclosed in U.S. Pat. No. 5,176,951.

Referring to FIG. 1, a photographic enlargement of a portion of a prior art commercial dental reinforcing ribbon material 10 made by the assignee of U.S. Pat. No. 5,176,951 in accordance therewith, showing a leno weave. In the material 10, a plurality of warps 11 run parallel to the longitudinal or lengthwise extent of the ribbon of the material 10, while a plurality of wefts 12 run transverse the warps 11 at right angles thereto. The longitudinal direction of the ribbon 10 is parallel to the arrow 10a in FIG. 1. The warps 11 are formed of twisted pairs of fiber filaments 13 between which the wefts 12 pass. The material 10 is approximately a 30×30 weave. The warps 11 are relatively taught and straight while the wefts 12 are relatively relaxed and capable of initially supporting little transverse tension, though it tends to transversely stretch with a memory, tending to return to its original width.

Figure 2:
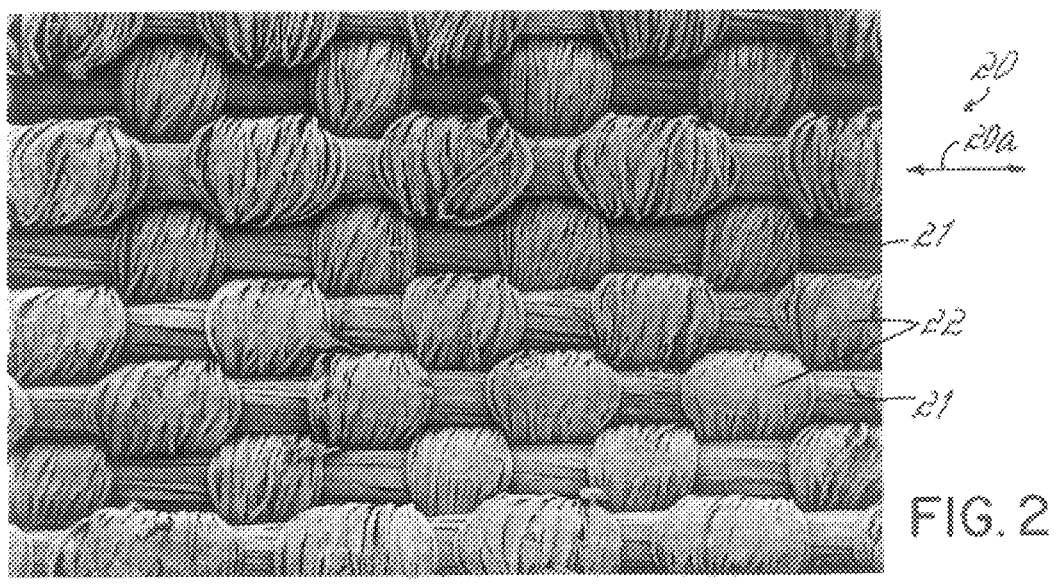
FIG. 2 is a SEM photographic enlargement of a plain weave reinforcing material having the tight weave features of the present invention.

FIG. 2 illustrates a plain weave material 20 embodying certain principles of the present invention. In the material 20, a plurality of warps 21 run parallel to the longitudinal or lengthwise extent of the ribbon of the material 20, while a plurality of wefts 22 run transverse the warps 21 at right angles thereto. In FIG. 2, the longitudinal direction of the ribbon 20 is parallel to the arrow 20a. The warps 21 are of a relatively tight weave, preferably 50×50 or greater, illustrated in FIG. 2 at about 55×55, which enhances the strength of the material. The warps 21 are taut and straight and the wefts 22 are also relatively taut, contributing to the multi-dimensional strength of the material 20 early in a loading process.

Figure 3:
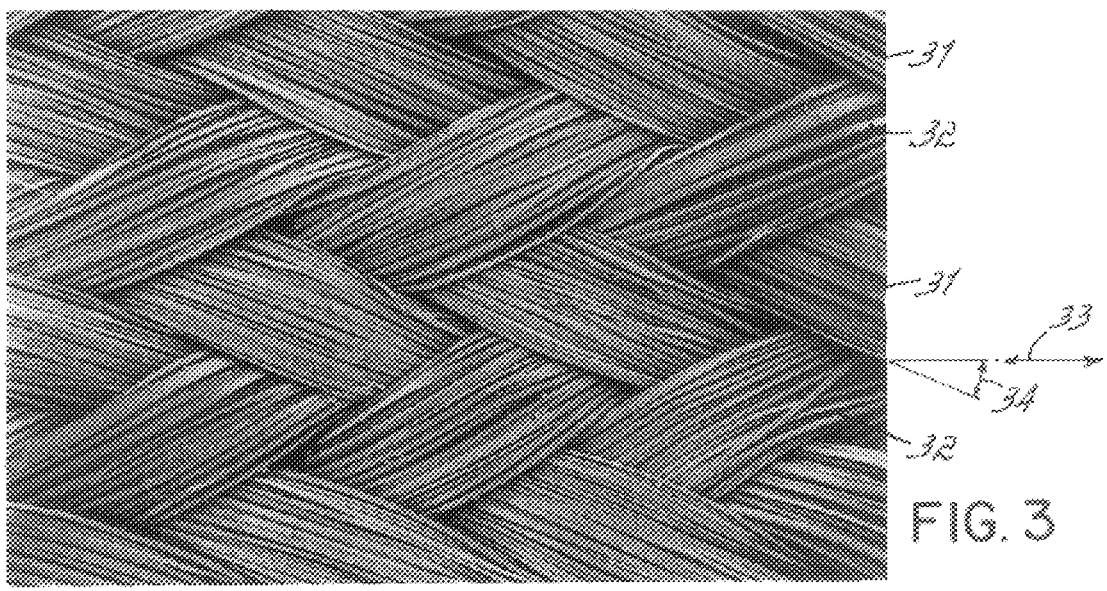
FIG. 3 is a SEM photographic enlargement of a braided weave reinforcing material according to one preferred embodiment of the present invention.
Figure 6:
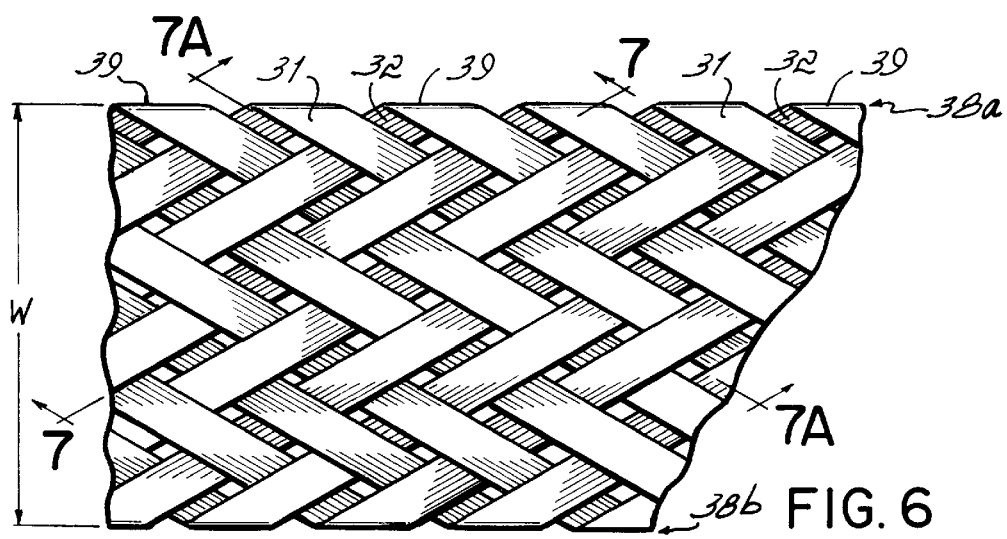
FIG. 6 is a view, similar to FIG. 4, illustrating a preferred edge pattern of a ribbon formed of the braided weave of FIG. 3.

FIG. 3 illustrates a material 30, according to the preferred embodiment of the invention, for use in combination with resins or combinations of resins such as manufactured by Kerr Corporation under its trademarks HERCULITE composite resin and KOLOR PLUS low viscosity resin, for use in tooth restorative procedures and in tooth straightening and reconstruction appliances and prostheses in orthodontics, periodontics and dentistry. The material 30 is formed of a braid or braided weave of fibers of high strength polymer that may be locally considered as including an array of alternating sets of parallel yarns 31 and 32, each oriented at an angle 34, illustrated at about 35°, of the same magnitude but opposite direction relative to the longitudinal or lengthwise extent or axis 33 of a ribbon into which the material is formed. Such a braid is formed on a braiding machine from fibers or ends of continuous filament yarn that are combined on an odd number of carriers, with each fiber alternately forming a yarn 31 of one set and then a yarn 32 of the opposing or crossing set, reversing its angle with the axis 33 at the respective edges 38a and 38b (FIG. 6) of the ribbon. Such a ribbon 30 is preferably not cut into the desired ribbon widths but is braided separately to each desired width. The width W is illustrated in FIG. 6 as the distance in the transverse direction between the edges 38a and 38b, which is generally in a range of from one to five millimeters. As illustrated in FIG. 3, the braid is preferably in a flat braid having a two-over/two-under weave pattern.

In the preferred embodiment of the invention, the material is provided in the shape of a ribbon having a longitudinal or lengthwise extent, with the fibers crossing at an angle of in the range of from 40° to 90° to each other, but preferably from about 50° to 75° to each other. The yarns are preferably high tenacity, ultra high molecular weight, gel spun continuous filament polyethylene fiber, such as Spectra® fiber produced by Allied Signal, Inc., although other high strength plastics such as aramids, as for example Kevlar®, a poly p-phenyleneterephthalamide fiber made by Dupont, may be used. The illustrated embodiment is a 3 mm wide ribbon formed of 17 ends, for example, of 215 denier Spectra® fiber, 125SFB17 Spectra®, 18 PPI, in a two over two under flat braid pattern.

Figure 4:
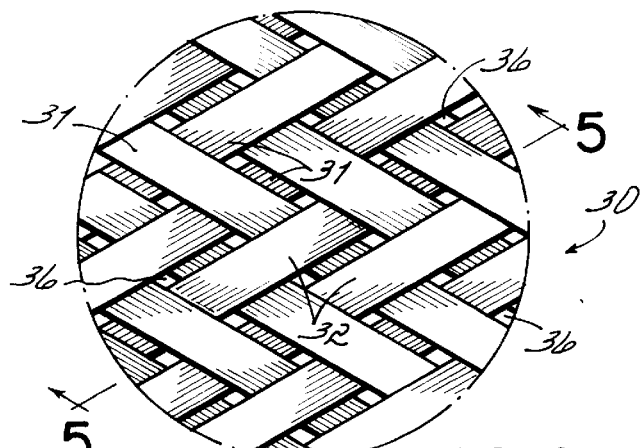
FIG. 4 is a diagram representing the braid pattern of the material of FIG. 3.
Figure 5:
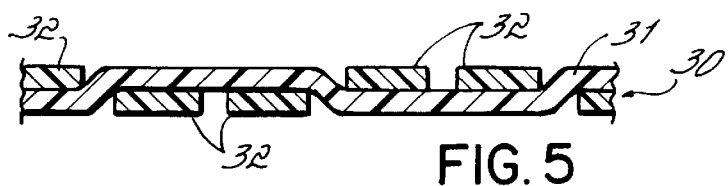
FIG. 5 is a cross-sectional view along line 5—5 of FIG. 4.

FIG. 4 is a diagrammatic representation of the weave pattern of the material 30, showing the fibers 31 passing over two fibers 32 and then under two fibers 32. This is further illustrated in the cross-sectional view of FIG. 5. Such a braid leaves a plurality of holes 36 between the fibers that facilitate the penetration of the material 30 with resin. The fibers 31 are parts of the same yarns that form the fibers 32 at longitudinally spaced intervals along the ribbon of material 30. Such yarns change transverse direction alternately at the respective edges of the ribbon of material 30, as illustrated at the edge 38a in FIG. 6, where the opposing fibers 31 and 32 which are parts of the same yarn are differentiated at a fold 39 in the yarn. This is further illustrated in the cross-sectional views of FIGS. 7. and 7A.

Figure 7:
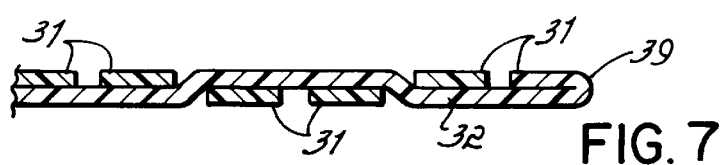
FIG. 7 is a cross-sectional view along line 7—7 of FIG. 6.
Figure 7A:
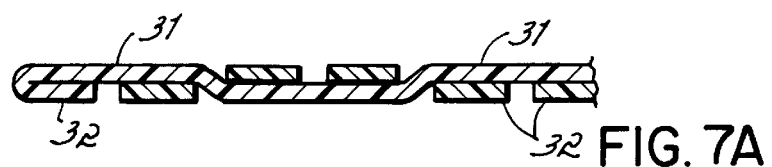
FIG. 7A is a cross-sectional view similar to FIG. 7. along line 7A—7A of FIG. 6.
Figure 8:
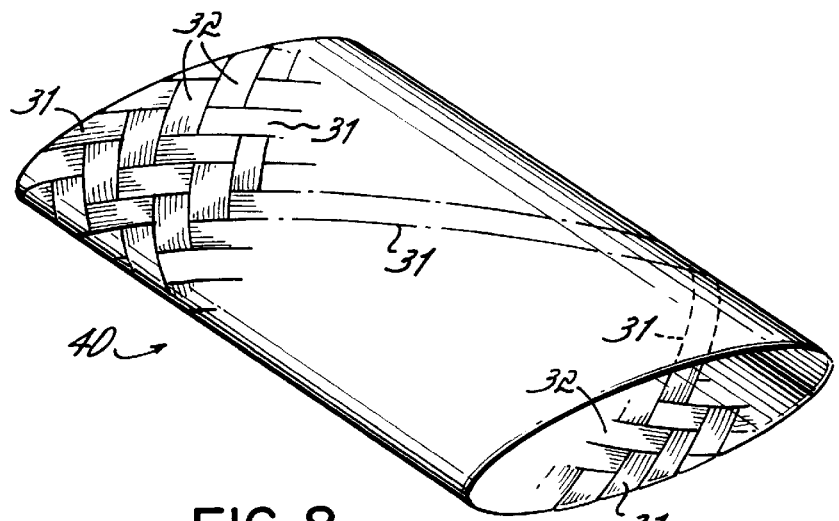
FIG. 8 is a perspective view of a tubular alternative to the ribbon of FIG. 6.

An alternative form of ribbon to that of FIGS. 6, 7 and 7A is in the ribbon 40 of FIG. 8, which is in the form of a fabric tube of the material 30. In such a ribbon 40, instead of the flat braid with the fibers 31 and 32 reversing at edges 38, the opposing fibers 31 and 32 each remain in distinct parallel sets throughout the length of the ribbon and spiral around a seamless tube of the material, with the set of fibers 31 spiraling clockwise and the set of fibers 32 spiraling counterclockwise around the tube. Such a tube is flattened to form the ribbon 40 having two layers formed of opposite sides of the tube. Such a tubular braid is formed with a different set up of a braiding machine than forms the flat braided material 30 of FIGS. 6, 7 and 7A.

The reinforcing materials 20, 30 or 40 are preferably treated with a cold plasma or by some other chemical, electrical, electro-chemical or physical or chemical vapor treatment process that will activate surface atoms to render the fibers more amenable to bonding with the resin. The treated fibers should be protectively packaged and handled to prevent contaminating contact of their treated surfaces that will expend the activated surface particles and negate or neutralize the treatment. Surface activation by plasma treatment is discussed in articles by S. L. Kaplan, et al., entitled "Plasma Surface Treatment of Plastics to Enhance Adhesion: An Overview", *Technical Notes*, Plasma Science, Inc., (February 1990) and "Gas Plasma Treatment of Spectra® Fiber, *Technical Notes*, Plasma Science, Inc., (March 1988).

Figure 9:
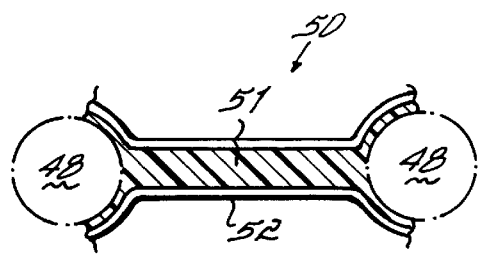
FIG. 9 is an occlusal view of a test sample dental bridge used in testing the materials of the invention.

Testing the above described reinforcing materials 10 of the prior art and 20 and 30 of the present invention has been carried out by constructing three-unit dental bridges, using each of the materials, in a three point flexural strength test similar to that of ISO 4049. The dental bridge was designed for a mandibular arch spanning the second molar to the first bicuspid with 13 mm between the prepared surfaces 48, simulating the crowns of the teeth between which the bridge would span. Such a bridge 50 is illustrated in FIG. 9. One set of bridges was constructed as a control for the tests from HERCULITE™ enamel composite resin, manufactured by Kerr Corporation. Other sets of bridges were constructed using HERCULITE enamel as a composite core 51 and then laminating the core 51 with a with skin 52 formed of a respective one of the reinforcing materials 10, 20 and 30. Application of the laminates was carried out by cutting lengths of ribbons of the respective materials and soaking the material first in low viscosity KOLOR PLUS™ resin, manufactured by Kerr Corporation, and then laminated over the composite core using HERCULITE enamel, with the axes of the ribbons extending lengthwise on the surface of the bridge core. Two overlapping layers of the material was used to completely cover the core.

The results of such tests showed the prior art material 10 approximately doubled the total energy required before total failure of the bridge, as compared to the control bridge, but that the average maximum force prior to failure increased about twelve percent. The test results for the tight woven material 20 and braided material 30 were almost equal in strength, nearly tripling the total energy required before failure of the bridge and nearly doubling the maximum force required for failure. Furthermore, with the braided material 30, substantial ease in wetting the material with resin was experienced in combination with a substantial ease in conforming the wetted material to the desired shape when laminating the reinforcement material onto the bridge.

Figure 10:
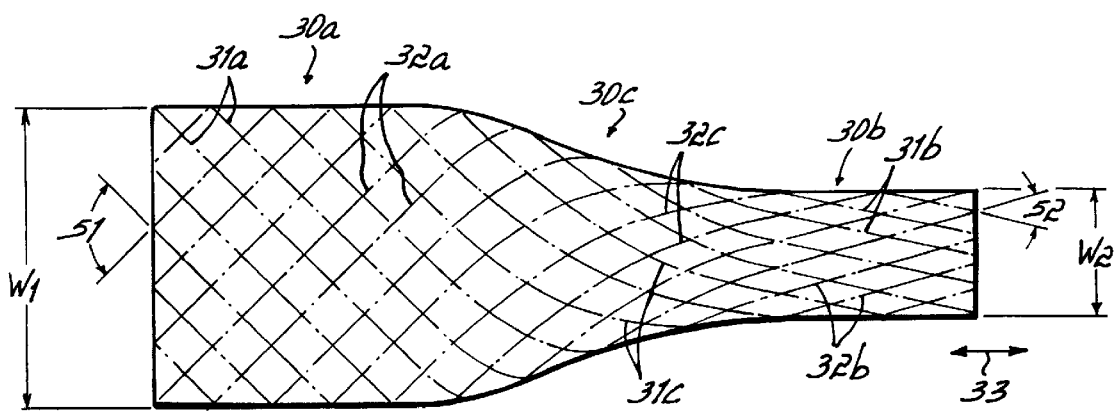
FIG. 10 is a diagramatic representation of a portion of a ribbon illustrating the angles of the crossing fibers with different portions of the ribbon adjusted to different widths.
Figure 11:
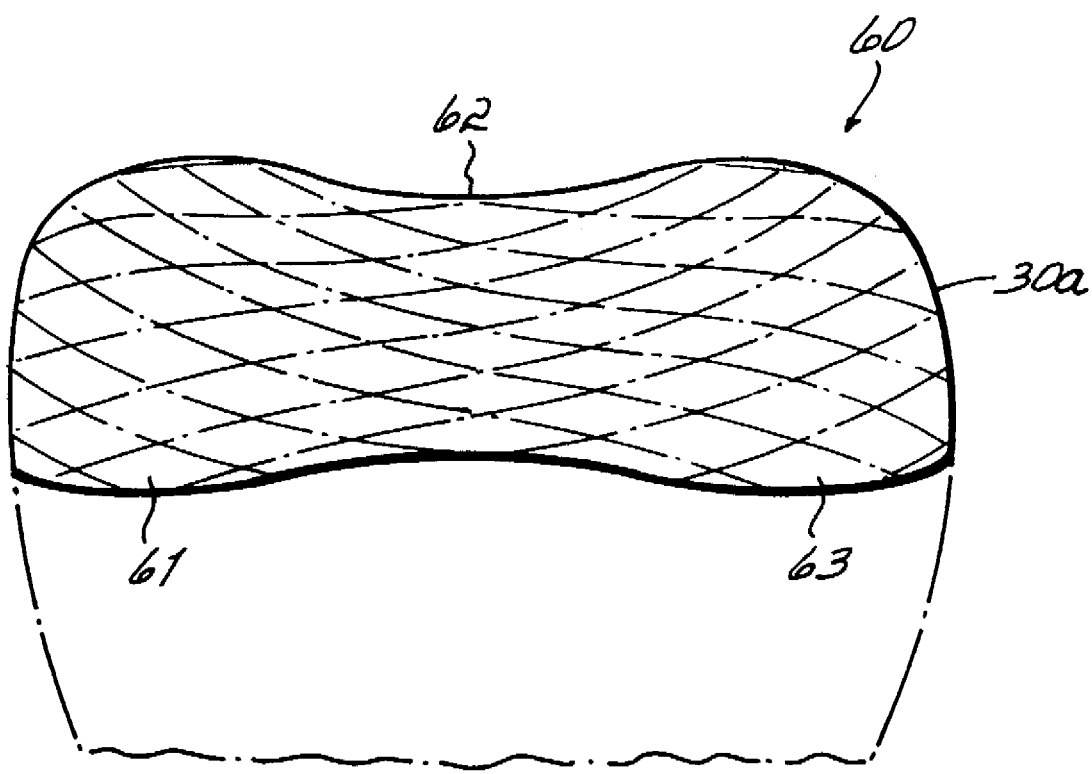
FIG. 11 is a diagramatic representation of the portion of a ribbon of FIG. 10 utilizing the variable width feature to conform to portions or a dental crown being reinforced therewith.

FIGS. 10 and 11 are diagrammatic illustrations showing how the orientation of fibers relative to the longitudinal extent 33 of the ribbon, for example ribbon 30, change to facilitate adjustment of the width of the ribbon. In FIG. 10, a portion 30a of the ribbon is shown with its width adjusted to cover the width $W_1$ a wide portion of a prosthesis to be reinforced. For example, the portion 30a of a nominally 3 mm wide ribbon is illustrated as widened to approximately 4 mm, which is accommodated by a longitudinal shorting of the widened portion 30a of the ribbon and an increase of the angle 51 of the crossing sets of fibers 31a and 32a about the longitudinal extent 33 of the ribbon. Another portion 30b of the ribbon is shown longitudinally stretched, with the crossing fibers 31b and 32b crossing at a narrow angle 52, thereby reducing the width of the portion 30b to a narrow width $W_2$, for example to 2 mm. Such a ribbon can be adjusted differently at different portions of its length, as illustrated. A widen portion 30a of the ribbon may be formed by the practitioner pulling transversely across the width of the ribbon to cause the fibers 31a and 32a to orient at the angle 51 to the longitudinal extent 33. Then, another portion 30b may be narrowed by the practitioner pulling longitudinally only across the portion of the ribbon to be narrowed to cause the fibers 31b and 32b to orient at the smaller angle 52 to the longitudinal extent 33 of the ribbon. In the portion of the ribbon 30c that interconnects the portions 30a and 30b, the fibers 31c and 32c curve in transition from the angle 51 to the angle 52. Such a ribbon of multiple adjusted widths is shown in FIG. 11 reinforcing a dental crown 60, with different portions 61, 62 and 63 conforming to different widths of the portion of the crown 60 to be reinforced.

Those skilled in the art will appreciate that the application of the present invention herein are varied, and that the invention is described in preferred embodiments Accordingly, additions and modifications can be made without departing from the principles of the invention. Accordingly, the following is claimed:

It is claimed:

1. A dental-reinforcing fabric having a long lengthwise extent and a narrow transverse extent and formed into a flat ribbon of continuous fibers of ultra high strength plastic material each extending in a zigzag pattern along the lengthwise extent of the fabric and interwoven in a braided over/under weave in alternating directions each oriented diagonally to the lengthwise extent of the ribbon thereby permitting adjustment to widen the transverse extent of the ribbon while its lengthwise extent shortens or narrow the transverse extent of the ribbon while its lengthwise extent lengthens.

2. The dental-reinforcing fabric ribbon of claim 1 having a long lengthwise extent and a narrow transverse extent and formed of fibers of reinforcing material configured and oriented to permit transverse adjustment of the width of the ribbon.

3. The ribbon of claim 2 wherein the reinforcing material is ultra high strength plastic material.

4. The ribbon of claim 2 wherein the ribbon has transverse edges and the fibers change direction at the edges of the ribbon.

5. The ribbon of claim 2 wherein substantially all of the fibers are oriented at a substantial angle to the transverse extent of the ribbon.

6. The ribbon of any of claims 3 through 5 wherein the ultra high strength plastic material is a high modulus, high molecular weight, highly oriented, extended chain polyethylene.

7. The ribbon of claim 6 wherein the fibers are surface activated fibers.

8. The ribbon of claim 7 wherein the surface activated fibers are plasma treated fibers.

9. The ribbon of claim 2 wherein the ribbon has a width generally in the range of of from 1 to 5 millimeters.

10. The ribbon of claim 2 wherein the ribbon is formed of a tight weave.

11. The dental reinforcing fabric of claim 1 wherein the fibers are oriented at an angle of between approximately 25° and approximately 45° to the longitudinal extent of the ribbon.

12. The dental reinforcing fabric of claim 1 wherein the fibers are interwoven in a flat braided weave.

13. The dental reinforcing fabric of claim 1 wherein the fibers are interwoven in a tubular braided weave and formable into a flat ribbon of two layers interconnected along the edges.

14. A method of fabricating a reinforced dental restoration having a width that varies along its length, the method comprising the steps of:

providing a flat dental-reinforcing fabric ribbon having a long lengthwise extent and a narrow transverse extent and formed of fibers of ultra high strength material interwoven in a braided over/under weave and oriented diagonally each at an angle to the lengthwise extent of the ribbon;

combining the ribbon with a settable resin in the shape of the prostheses being fabricated;

adjusting the width of the ribbon to conform to at least a portion of the surface of the restoration and thereby increasing or decreasing the angles of the fibers to the lengthwise extent of the ribbon as the width is respectively increased or decreased as the length is shortened where the width is increased and lengthened where the width is decreased; and setting the resin to form at least part of the restoration.

15. The method of claim 14 wherein the ribbon providing step includes the step of braiding the fibers.

16. The method of claim 14 wherein the ribbon providing step includes the steps of providing the ribbon having fibers of high modulus, high molecular weight, highly oriented, extended chain polyethylene.

17. The method of claim 14 wherein the ribbon providing step includes the step of activating the surfaces of the fibers of the ribbon.

18. A dental restoration formed according to the method of any of claims 14 through claim 17.

19. The method of claim 14 wherein the ribbon providing step includes the step of providing the ribbon comprised of a plastic material.

* * * * *